United States Patent [19]

Bourzat et al.

[11] Patent Number: 5,338,760
[45] Date of Patent: Aug. 16, 1994

[54] UREA DERIVATIVES, THEIR PREPARATION AND MEDICINAL PRODUCTS CONTAINING THEM

[75] Inventors: Jean-Dominique Bourzat, Vincennes; Marc Capet, Thiais; Claude Cotrel, Paris; Claude Guyon, Saint-Maur des Fosses; Franco Manfre, Vitry sur Seine; Gérard Roussel, Soisy sur Seine, all of France

[73] Assignee: Rhone-Poulenc Rorer S.A., Antony Cedex, France

[21] Appl. No.: 934,686

[22] PCT Filed: Mar. 11, 1991

[86] PCT No.: PCT/FR91/00195
§ 371 Date: Sep. 11, 1992
§ 102(e) Date: Sep. 11, 1992

[87] PCT Pub. No.: WO91/13862
PCT Pub. Date: Sep. 19, 1991

[30] Foreign Application Priority Data

Mar. 13, 1990 [FR] France ................ 90 03187

[51] Int. Cl.[5] .................... C07C 229/26; A61K 31/13
[52] U.S. Cl. ..................... 514/539; 560/34; 560/9

[58] Field of Search .......... 560/9, 43, 38, 39, 41, 560/34; 514/535, 549

[56] References Cited

FOREIGN PATENT DOCUMENTS 397556 5/1990 European Pat. Off.

Primary Examiner—Jose' G. Dees
Assistant Examiner—Samuel Barts
Attorney, Agent, or Firm—Morgan & Finnegan

[57] ABSTRACT

Compounds of formula:

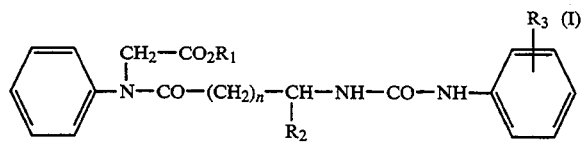

in which $R_1$ represents an alkyl radical, $R_2$ represents a phenyl radical or a chain $-(CH_2)_m-R_4$ in which m is equal to 0, 1 or 2 and R, represents a hydroxyl, alkoxy or amino radical, $R_3$ represents a hydrogen atom or an alkyl, alkoxy or alkylthio radical and n is equal to 0 or 1, their preparation and medicinal products containing them.

7 Claims, No Drawings

UREA DERIVATIVES, THEIR PREPARATION AND MEDICINAL PRODUCTS CONTAINING THEM

The present invention relates to compounds of formula

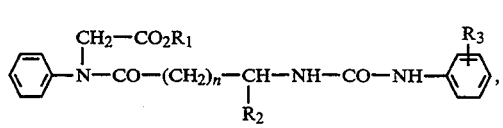

to their preparation and to medicinal products containing them.

In the formula (I):

$R_1$ represents an alkyl radical, $R_2$ represents a phenyl radical or a chain $-(CH_2)_m-CO-R_4$ in which m is equal to 0, 1 or 2 and $R_4$ represents hydroxyl, alkoxy or amino radical, $R_3$ represents a hydrogen or halogen atom or an alkyl, alkoxy or alkylthio radical, and n is equal to 0 or 1

In the foregoing definitions and those which will be mentioned below, except where otherwise stated, the alkyl and alkoxy radicals contain 1 to 4 carbon atoms in a straight or branched chain.

In the formula (I), the halogen atoms are preferably chlorine, bromine or fluorine atoms.

The racemates and enantiomers of the compounds of formula (I) form part of the invention.

The compounds of formula (I) for which $R_2$ represents a phenyl radical or a chain $-(CH_2)_m-CO-R_4$ in which m is equal to 0, 1 or 2 and $R_4$ represents an alkoxy radical may be obtained by the action of an amine of formula:

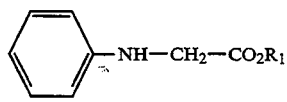

in which $R_1$ has the same meanings as in the formula (I), on an acid of formula:

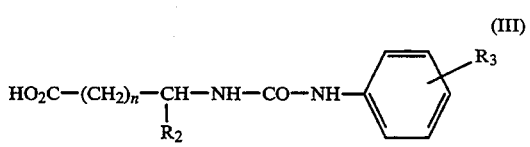

in which n and $R_3$ have the same meanings as in the formula (I) and $R_2$ has the same meanings as above, or a reactive derivative of this acid.

When the acid is employed, the reaction is performed in the presence of a peptide-condensing agent such as a carbodiimide (e.g. dicyclohexylcarbodiimide) or N,N'-carbonyldiimidazole in an inert solvent such as an ether (e.g. THF, dioxane), an amide (e.g. DMF) or a chlorinated solvent (e.g. methylene chloride, 1,2-dichloroethane, chloroform) at a temperature between 0° C. and the refluxing temperature of the reaction mixture.

When a reactive derivative of the acid is employed, it is possible to react the anhydride, a mixed anhydride, an acid halide or an ester (which may be selected from the activated or unactivated esters of the acid).

The reaction is then performed either in an organic medium, optionally in the presence of an acceptor for acid such as a nitrogenous organic base (e.g. a trialkylamine, a pyridine, 1,8-diazabicyclo[5.4.0]undec-7-ene or 1,5-diazabicyclo[4.3.0]non-5-ene), in a solvent such as is mentioned above or a mixture of these solvents, at a temperature of between 0° C. and the refluxing temperature of the reaction mixture, or in a two-phase aqueous-alcoholic medium in the presence of an alkali metal or alkaline-earth metal base (sodium hydroxide. potassium hydroxide) or alkali metal or alkaline-earth metal carbonate or bicarbonate at a temperature of between 0° and 40° C.

The amines of formula (II) may be obtained by the action of aniline on a derivative of formula:

in which $R_1$ has the same meanings as in the formula (I) and Hal represents a halogen atom (preferably chlorine or bromine).

This reaction is preferably performed in an inert solvent such as acetonitrile, dimethylformamide or tetrahydrofuran, at the boiling point of the solvent.

The derivatives of the formula (IV) may be obtained by application or adaptation of the methods described in Beilstein 2,213 and 2,197.

The acids of formula (III) may be prepared by the action of a phenyl isocyanate of formula:

in which $R_3$ has the same meanings as in the formula (I), on a derivative of formula:

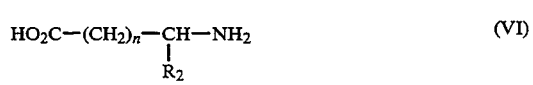

in which n has the same meanings as in the formula (I) and $R_2$ represents a phenyl radical or a chain $-(CH_2)_m-CO-R_4$ in which m is equal to 0, 1 or 2 and $R_4$ represents an alkoxy radical.

This reaction is generally performed in an inert solvent such as tetrahydrofuran, dimethylformamide, a chlorinated solvent (e.g. chloroform, 1,2-dichloroethane) or an aromatic solvent (e.g. benzene, toluene), at a temperature between 10° C. and the boiling point of the solvent.

The isocyanates of formula (V) may be obtained by application or adaptation of the method described by R. Richter et al., The Chemistry of Cyanates and their thio derivatives, S. Patai, part 2, Wiley N.Y. (1977).

The derivatives of formula (V) for which $R_2$ represents a chain $-(CH_2)_m-CO-R_4$ in which $R_4$ represents an alkoxy radical may be obtained by application or adaptation of the method described by D. Coleman, J. Chem. Soc., 2294 (1951).

The compounds of formula (I) for which $R_2$ represents a chain $-(CH_2)_m-CO-R_4$ in which $R_4$ represents a hydroxyl radical may be prepared by hydrolysis of the corresponding compound of formula (I) for which $R_4$ represents an alkoxy radical.

This hydrolysis is generally performed by means of a base such as sodium hydroxide or potassium hydroxide, in an inert solvent such as water or an alcohol or a mixture of these solvents, at a temperature in the region of 20° C., followed by the action of an acid to release the product in acid form.

The compounds of formula (I) for which $R_2$ represents a chain —$(CH_2)_m$—CO—$R_4$ in which $R_4$ represents an amino radical may be obtained by the action of ammonia on the corresponding compound for which $R_4$ represents an alkoxy radical.

This reaction is generally performed in an alcohol such as methanol or ethanol at a temperature in the region of 25° C.

The enantiomers of the compounds of the formula (I) may be obtained by resolution of the racemates, e.g. by chromatography on a chiral column according to W. H. Pirckle et al., Asymmetric Synthesis, Vol. 1, Academic Press (1983), or by synthesis from chiral precursors.

The compounds of formula (I) may be purified by the usual known methods, e.g. by crystallisation, chromatography, extraction, etc.

The compounds of formula (I) for which $R_4$ represents a hydroxyl radical may be converted to metal salts or to addition salts with nitrogenous bases according to methods known per se. These salts may be obtained by the action of a metallic base (e.g. an alkali metal or alkaline-earth metal base), ammonia or an amine on a compound of formula (I), in a solvent such as an alcohol, an ether or water, or by an exchange reaction with a salt of an organic acid. The salt formed is separated by the usual methods.

These salts also form part of the invention.

As examples of pharmaceutically acceptable salts, the salts with alkali metals (sodium, potassium, lithium) or with alkaline-earth metals (calcium, magnesium), the ammonium salt and the salts of nitrogenous bases (ethanolamine, triethylamine, methylamine, benzylamine, N-benzyl-β-phenethylamine, choline, arginine, leucine, lysine, N-methylglucamine) may be mentioned.

The compounds of formula (I) display advantageous pharmacological properties. These compounds possess a strong affinity for cholecystokinin (CCK) receptors and gastrin receptors, and are hence useful in the treatment and prevention of disorders linked to CCK and gastrin at nervous system and gastrointestinal system level.

Thus, these compounds may be used for the treatment or prevention of psychoses, anxiety disorders, Parkinson's disease, tardive dyskinesia, irritable colon syndrome, acute pancreatitis, ulcers, disorders of intestinal motility and some tumours of the lower oesophagus, colon and intestine, and as an appetite regulator.

These compounds also have a boosting effect on the analgesic activity of narcotic and non-narcotic medicinal products.

The affinity of the compounds of formula (I) for CCK receptors was determined according to a technique based on that of A. Saito et al., J. Neuro. Chem., 37, 483–490 (1981) at cerebral cortical level and at pancreatic level.

In these tests, the $IC_{50}$ of the compounds of formula (I) does not generally exceed 1000 nM.

Moreover, it is known that products which recognise central CCK receptors have a similar specificity for the gastrin receptors in the gastrointestinal tract (Bock et al., J. Med. Chem., 32, 16–23 (1989), Reyfeld et al., Am. J. Physiol., 240, G255–266 (1981); Beinfeld et al., Neuropeptides, 3, 411–427 (1983)).

The compounds of the formula (I) display low toxicity. Administered subcutaneously in mice, their $LD_{50}$ is generally greater than 40 mg/kg.

Preferred compounds are those for which $R_1$ represents a tert-butyl radical.

The following compounds are of special interest:
tert-butyl (RS)-2-{3-[3-)3-methylphenyl)ureido]3-phenyl-N-phenyl propionamido}acetate,
methyl (RS)-3-[3-(3-methylphenyl)ureido]-N-(tert-butoxycarbonylmethyl)-N-phenylsuccinamate,
(RS)-3-[3-(3-methylphenyl)ureido]-N-(tertbutoxycarbonylmethyl)-N-phenylsuccinamic acid,
(RS)-2-[3-(3-methylphenyl)ureido]-N-(tertbutoxycarbonylmethyl)-N-phenylsuccinamide,
methyl (RS)-4-[3-(3-methylphenyl)ureido]-N-(tert-butoxycarbonylmethyl)-N-phenylglutaramate,
(RS)-4-[3-(3-methylphenyl)ureido]-N-(tertbutoxycarbonylmethyl)-N-phenylglutaramic acid.

The examples which follow illustrate the invention without limiting the latter.

EXAMPLE 1

A suspension of tert-butyl anilinoacetate (4.1 g) and (R,S)-3-[3-(3-methylphenyl)ureido]3-phenylpropionic acid (5.97 g) in anhydrous 1,2-dichloro-ethane (50 cc) is heated to reflux. Thionyl chloride (1.45 cc) is then added while refluxing is maintained until the gaseous evolution has ceased. The reaction mixture is then poured into a saturated aqueous sodium hydrogen carbonate solution (30 cc) and thereafter methylene chloride (50 cc) is added. The organic phase is washed with water (50 cc), dried over magnesium sulphate and concentrated to dryness under reduced pressure (2.7 kPa) at 40° C. After two successive recrystallisations, first in a mixture of diethyl ether and diisopropyl ether (50: 50 by volume) and then in diethyl ether, tert-butyl (RS)-2-{3-[3-(3-methylphenyl)ureido]-3-phenyl-N-phenylpropionamido}acetate (5.4 g) is obtained.

(RS)-3-[3-(3-Methylphenyl)ureido]-3-phenylpropionic acid may be prepared in the following manner: 3-methylphenyl isocyanate (5.14 cc) is added in the course of 1 minute to a suspension of (RS)-3-amino-3-phenylpropionic acid (6.6 g) and sodium hydrogen carbonate (3.36 g) in water (100 cc). The mixture is stirred for 20 hours at a temperature in the region of 20° C. and is then extracted with ethyl acetate (3×75 cc). The organic phase is washed with water (2×50 cc) and the aqueous extracts are combined and acidified to pH 1 with 4N aqueous hydrochloric acid solution. The precipitate is filtered off, washed with water and dried under reduced pressure (0.07 kPa) at 40° C. (RS)-3-[3-(3-Methylphenyl)ureido]-3-phenylpropionic acid (8.7 g), m.p. 164° C., is thereby obtained.

EXAMPLE 2

Thionyl chloride (3.2 g) is added to a suspension of (RS)-2-[3-(3-methylphenyl)ureido]3-methoxycarbonylpropionic acid (7.5 g) and tert-butyl N-phenylglycinate (5.55 g) in 1,2-dichloroethane (500 cc) under reflux. The reaction medium is stirred for a further 15 minutes under reflux, then cooled to 50° C. and poured into 10% aqueous sodium bicarbonate solution (200 cc). The organic phase is separated after settling has taken place, washed with water (150 cc), dried over magnesium sulphate and then concentrated under reduced pressure (2.7 kPa). The oily residue is purified by chromatography on silica (0.063–0.200 mm) (120 g) contained in a column 2.4 cm in diameter [eluent: methylene chloride/methanol (99.5: 0.5 by volume)], collecting 40-cc fractions. Fractions 20 to 56 are combined and concentrated to dryness under reduced pressure (2.7 kPa) at 50° C. After crystallisation in diethyl ether, methyl (RS)-3-[3-(3-methylphenyl)ureido]-N-tert-butoxycarbonylmethyl)-N-phenylsuccinamate (2.6 g), m.p. 149° C., is obtained.

(RS)-2-[3-(3-Methylphenyl)uriedo]-3-methoxycarbonylpropionic acid may be prepared in the following manner: 3-methylphenyl isocyanate (13.3 g) is added in the course of 30 minutes at 17° C. to a solution of (RS)-2-amino-3-methoxycarbonylpropionic acid (16.1 g) and sodium bicarbonate (8.4 g) in water (160 cc). The reaction medium is stirred for a further 16 hours and the insoluble matter is then filtered off. The liltrate is taken to pH 1 with 4N hydrochloric acid and extracted with ethyl acetate (3×15 cc). The extracts are combined, washed with water (2×15 cc), dried over magnesium sulphate and then taken to dryness under reduced pressure (2.7 kPa) at 70° C. After crystallisation in petroleum ether, (RS)-2-[3-(3-methylphenyl)ureido]-3-methoxycarbonylpropionic acid (24 g) is obtained.

(RS)-2-Amino-3-methoxycarbonylpropionic acid may be prepared according to the method described by D. Coleman, J. Chem. Soc., 2294 (1951).

EXAMPLE 3

Normal sodium hydroxide (7.5 cc) is added to a solution of methyl (RS)-3-[3-(3-methylphenyl)ureido]-N-tert-butoxycarbonylmethyl)-N-phenylsuccinamate (3.5 g) in methanol (120 cc). The reaction medium is stirred for 24 hours at a temperature in the region of 20° C. and the methanol is then evaporated off under reduced pressure (2.7 kPa) at 60 ° C. The residue is diluted with 0.005 N sodium hydroxide (210 cc). The aqueous phase is washed with ethyl acetate (2×70 cc), taken to an acid pH with 4N hydrochloric acid and extracted with ethyl acetate (3×80 cc). The organic extracts are combined, dried over magnesium sulphate and taken to dryness under reduced pressure (2.7 kPa) at 70° C. After crystallisation in diethyl ether, (RS)-3-[3-(3-methylphenyl)ureido]-N-(tertbutoxycarbonylmethyl)-N-phenylsuccinamic acid (1.6 g), m.p. 198° C., is obtained.

EXAMPLE 4

A stream of ammonia is passed for 11 hours at a temperature in the region of 25° C. into a solution of methyl (RS)-3-[3-(3-methylphenyl)ureido]-N-(tertbutoxycarbonylmethyl)-N-phenylsuccinamate (4.7 g) in methanol (150 cc). The solution is then outgassed with a stream of nitrogen and concentrated under vacuum (2.7 kPa) at 60° C. The residue is crystallised in diethyl ether and the solid extracted with dichloromethane (40 cc). The solution thereby obtained is purified by chromatography on silica (0.063–0.200 mm) (25 g) contained in a column 1.6 cm in diameter [eluent: methylene chloride (1100 cc), then methylene chloride/methanol (98.5:1.5 by volume)], collecting 15-cc fractions. Fractions 80 to 127 are combined and concentrated to dryness under reduced pressure (2.7 kPa) at 60° C. After crystallisation in petroleum ether, (RS)-2-[3-(3-methylphenyl)ureido]-N-(tert-butoxycarbonylmethyl)-N-phenylsuccinamide (1.1 g), m.p. 192° C., is obtained.

EXAMPLE 5

The procedure is similar to that described in Example 2, but starting with (RS)-2-[3-(3methylphenyl)ureido]-4-methoxycarbonylbutyric acid (1.47 g), tert-butyl N-phenylglycinate (1.04 g) and thionyl chloride (0.60 g). The product obtained is purified by chromatography on silica (0.063–0.200 mm) (50 g) contained in a column 1.8 cm in diameter [eluent: methylene chloride (225 cc), then methylene chloride/methanol (99: 1 by volume)], collecting 15-cc fractions. Fractions 36 to 40 are combined and concentrated to dryness under reduced pressure (2.7 kPa) at 50° C. After recrystallisation in diethyl ether followed by recrystallisation in a mixture of hexane and ethanol (85:15 by volume), methyl (RS)-4-[3-(3-methylphenyl)ureido]-N-tert-butoxycarbonylmethyl)-N-phenylglutamate (1.9 g), m.p. 139° C., is obtained.

(RS)-2-[3-(3-Methylphenyl)ureido]-4-methoxycarbonylbutyric acid may be prepared in a manner similar to that described in Example 2 for the preparation of (RS)-2-[3-(3-methylphenyl)ureido]-3-methoxycarbonylpropionic acid, but starting with (RS)-2-amino-4-methoxycarbonylbutyric acid (16.1 g) and 3-methylphenyl isocyanate (13.3 g). (RS)-2-[3-(3-Methylphenyl)ureido]-4-methoxycarbonylbutyric acid (23.5 g), m.p. 127° C., is thereby obtained.

EXAMPLE 6

The procedure is as in Example 3, but starting with methyl (RS)-4-[3-(3-methylphenyl)ureido]-N-(tert-butoxycarbonylmethyl)-N-phenylglutaramate (4.7 g) and normal sodium hydroxide (9.7 cc). The product obtained is purified by chromatography on silica (0.063–0.200 mm) (60 g) contained in a column 2.4 cm in diameter [eluent: methylene chloride/methanol (99: 1 by volume) (1000 cc), then methylene chloride/methanol (97:3 by volume)], collecting 25-cc fractions. Fractions 42 to 105 are combined and concentrated to dryness under reduced pressure (2.7 kPa) at 60° C. After crystallisation in diethyl ether, (RS)-4-[3-(3-methylphenyl) ureido]-N-(tertbutoxycarbonylmethyl)-N-phenylglutaramic acid (1.45 g), m.p. 191° C., is obtained.

The present invention also relates to medicinal products consisting of at least one compound of formula (I), in the pure state or in the form of a composition in which it is combined with any other pharmaceutically compatible product which can be inert or physiologically active. The medicinal products according to the invention may be employed orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica. These compositions can also comprise substances other than diluents, e.g. one or more lubricants such as magnesium stearate or talc, a colouring, a coating (dragees) or a varnish.

As liquid compositions for oral administration, pharmaceutically acceptable solutions, suspensions, emulsions, syrups and elixirs, containing inert diluents such as water, ethanol, glycerol, vegetable oils or liquid paraffin, may be used. These compositions can comprise substances other than diluents, e.g. wetting products, sweeteners, thickeners, flayoutings or stabilisers.

The sterile compositions for parenteral administration can preferably be suspensions, emulsions, aqueous solutions or non-aqueous solutions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity agents, emulsifiers, dispersants and stabilisers. The sterilisation may be carried out in several ways, e.g. by aseptic filtration, by incorporating sterilising agents in the composition, by irradiation or by heating. They may also be prepared in the form of sterile solid compositions which can be dissolved at the time of use in a sterile injectable medium.

The compositions for rectal administration are suppositories or rectal capsules which contain, apart from the active product, excipients such as cocoa butter, semi-synthetic glycerides or polyethylene glycols.

The compositions for topical administration can be, e.g. creams, ointments, lotions, eye washes, mouth washes, nasal drops or aerosols.

In human therapy, the compounds according to the invention are especially useful in the treatment and prevention of disorders linked to CCK and gastrin at nervous system and gastrointestinal system level. These compounds can hence be used in the treatment and prevention of psychoses, anxiety disorders, Parkinson's disease, tardive dyskinesia, irritable colon syndrome, acute pancreatitis, ulcers, disorders of intestinal motility and some tumours of the lower oesophagus, colon and intestine, as an agent for boosting the analgesic activity of narcotic and non-narcotic analgesic medicinal products and as an appetite regulator.

The doses depend on the effect sought, the treatment period and the administration route used; generally between 0.05 g and 1 g per day, administered orally, for an adult, with single doses ranging from 10 mg to 500 mg of active substance.

Generally speaking, the doctor will determine the appropriate dosage in accordance with the age and weight and all other factors characteristic of the subject to be treated.

The examples which follow illustrate compositions according to the invention:

EXAMPLE A

Hard gelatin capsules containing 50 mg of active product and having the following composition are prepared according to the usual technique:

| | |
|---|---|
| tert-Butyl (RS)-2-{3-[3-(3-methyl-phenyl)ureido]-3-phenyl-N-phenyl-propionamido}acetate | 50 mg |
| Cellulose | 18 mg |
| Lactose | 55 mg |
| Colloidal silica | 1 mg |
| Carboxymethylstarch sodium | 10 mg |
| Talc | 10 mg |
| Magnesium stearate | 1 mg |

EXAMPLE B

Tablets containing 50 mg of active product and having the following composition are prepared according to the usual technique:

| | |
|---|---|
| Methyl (RS)-3-[3-(3-methylphenyl)-ureido]-N-(tert-butoxycarbonylmethyl)-N-phenylsuccinamate | 50 mg |
| Lactose | 104 mg |
| Cellulose | 40 mg |
| Polyvidone | 10 mg |
| Carboxymethylstarch sodium | 22 mg |
| Talc | 10 mg |
| Magnesium stearate | 2 mg |
| Colloidal silica | 2 mg |
| Mixture of hydroxymethylcellulose, glycerol and titanium oxide (72:3.5:24.5) | q.s. 1 finished film-coated tablet weighing 245 mg |

EXAMPLE C

An injectable solution containing 10 mg of active product and having the following composition is prepared:

| | |
|---|---|
| (RS)-3-[3-(3-Methylphenyl)-N-(tert-butoxycarbonylmethyl)-N-phenylsuccinamic acid | 10 mg |
| Benzoic acid | 80 mg |
| Benzyl alcohol | 0.06 cc |
| Benzoate | 80 mg |
| Ethanol, 95% | 0.4 cc |
| Sodium hydroxide | 24 mg |
| Propylene glycol | 1.6 cc |
| Water | q.s. 4 cc |

We claim:
1. A compound of formula

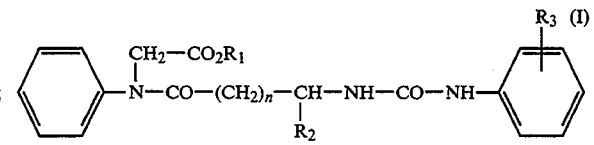

in which:
R$_1$ represents an alkyl radical,
R$_2$ represents a phenyl radical or a chain —(CH$_2$)$_m$—CO—R$_4$ in which m is equal to 0, 1 or 2 and R$_4$ represents a hydroxyl, alkoxy or amino radical,
R$_3$ represents a hydrogen or halogen atom or an alkyl, alkoxy or alkylthio radical, and
n is equal to 0 or 1, on the understanding that the alkyl and alkoxy radicals and alkyl portions contain 1 to 4 carbon atoms in a straight or branched chain, as well as its racemates and enantiomers and its salts.

2. A compound according to claim 1 for which R$_1$ represents a tert-butyl radical.

3. A compound according to one of claim 1 for which the halogen atoms are chlorine, bromine or fluorine atoms.

4. A process for preparing a compound of formula (I) according to claim 1 for which R$_2$ represents a phenyl radical or a chain —(CH$_2$)$_m$—CO—R$_4$ in which m is equal to 0, 1 or 2 and R$_4$ represents an alkoxy radical, wherein an amine of formula

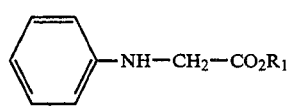

in which R$_1$ has the same meanings as in claim 1, is reacted with an acid of formula:

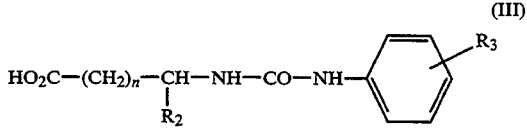

(III)

in which n and $R_3$ have the same meanings as in claim 1 and $R_2$ has the same meanings as above, or a reactive derivative of this acid, and the product is then isolated.

5. A process for preparing a compound of formula (I) according to claim 1 for which $R_2$ represents a chain —$(CH_2)_m$—CO—$R_4$ in which m is equal to 0, 1 or 2 and $R_4$ represents a hydroxyl radical, wherein the corresponding compound of formula (I) in which $R_4$ represents an alkoxy radical is hydrolysed and the product is then isolated.

6. A process for preparing a compound of formula (I) according to claim 1 for which $R_2$ represents a chain —$(CH_2)_m$—$R_4$ in which m is equal to 0, 1 or 2 and $R_4$ represents an amino radical, wherein ammonia is reacted with a corresponding compound of formula (I) for which $R_4$ represents an alkoxy radical and the product is then isolated.

7. A medicinal composition, which contains as active principle at least one compound of formula (I) according to claim 1 and a pharmaceutically acceptable carrier.

* * * * *